United States Patent [19]

Bell et al.

[11] Patent Number: 5,270,310
[45] Date of Patent: Dec. 14, 1993

[54] N-AMINOALKYL AMIDE INHIBITORS OF PROTEIN KINASE C

[75] Inventors: Robert M. Bell; Robert J. Fogelsong; Jeffrey B. Nichols, all of Durham, N.C.

[73] Assignees: Sphinx Pharmaceuticals Corporation; Duke University, both of Durham, N.C.

[21] Appl. No.: 807,084

[22] Filed: Dec. 13, 1991

[51] Int. Cl.$^5$ .............................................. A61K 31/33
[52] U.S. Cl. ................... 514/238.2; 514/255; 514/315; 514/331; 514/625; 544/168; 544/400; 546/233; 546/247; 564/215; 564/218
[58] Field of Search ............. 544/168, 400; 546/233, 546/247; 564/215, 218; 514/238.2, 255, 315, 331, 625

[56] References Cited

U.S. PATENT DOCUMENTS

| | | | |
|---|---|---|---|
| 2,220,508 | 4/1939 | Bock et al. | 91/70 |
| 2,303,191 | 11/1942 | Baldwin et al. | 260/295 |
| 4,816,450 | 3/1989 | Bell et al. | 514/25 |
| 4,874,604 | 10/1989 | Sramek | 424/47 |

FOREIGN PATENT DOCUMENTS

| | | |
|---|---|---|
| 0402266 | 12/1990 | European Pat. Off. |
| 2249471 | 10/1976 | Fed. Rep. of Germany |
| 2646199 | 10/1976 | Fed. Rep. of Germany |
| 3827974 | 8/1988 | Fed. Rep. of Germany |
| 47042486 | 12/1972 | Japan |
| 53035915 | 9/1978 | Japan |
| 01103663 | 7/1991 | Japan |
| 2220216 | 6/1988 | United Kingdom |

OTHER PUBLICATIONS

Yoshida et al., Chemical Abstracts, vol. 90, No. 24738f, 1979.
Castagna et al., J. Biol. Chem. 257:7847 (1982).
Grunicke et al., Adv. Enzyme Regul. 28:201 (1989).
Tritton, et al., Cancer Cells 2:95–102 (1990).
Schachtele et al., Biochem. Biophy. Res. Commun. 151: 542 (1988).
Hannun et al., J. Biol. Chem. 262:13620 (1987).
Yamada et al., Biochem. Pharmacol. 37:1161 (1988).
McIntyre et al., J. Biol. Chem. 262:15730 (1987).
Lambreth et al., J. Biol. Chem. 263:3818 (1988).
Pittet et al., J. Biol. Chem. 262:10072 (1987).
Gaudry et al., Immunology 63:715 (1988).
Wilson et al., J. Biol. Chem. 261:12616 (1986).
Fujita et al., Biochem. Pharmacol. 35:4555 (1986).
Berkow et al., J. Leukoc., Bioo. 41:441 (1987).
Salzer et al., Biochem. Biophys. Res. Commun. 148:747 (1987).
Kramer et al., J. Biol. Chem. 262:5876 (1989).
Dewald et al., Biochem. J. 264:879 (1989).
De Groot et al., Contact Dermatitis 19(4):289 (1988).
Khim-Farm. Zh. 15(2): 28 (1981).
Seifen, Ole, Fete, Waschse, 102(7):181 (1976).

*Primary Examiner*—Johann Richter
*Attorney, Agent, or Firm*—Woodcock Washburn Kurtz Mackiewicz & Norris

[57] ABSTRACT

The present invention provides methods for inhibiting protein kinase C which comprise contacting protein kinase C with an inhibitory amount of a compound having the formula

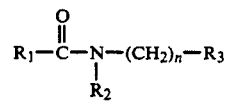

wherein $R_1$ is $C_8$ through $C_{15}$ alkyl; $R_2$ is H, $C_1$ through $C_{10}$ alkyl, or benzyl; $R_3$ is N-heterocyclic, N-alkyl-heterocyclic, quaternized N-heterocyclic, $NR_4R_5$ or $N^+R_4R_5R_6X^-$; $R_4$, $R_5$ and $R_6$ are independently $C_1$ through $C_{10}$ alkyl; n is 2, 3, 4, or 5; and X is an anion. The invention also provides novel compounds having the formula

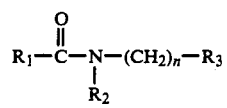

wherein $R_1$ is $C_8$ through $C_{15}$ alkyl; $R_2$ is H, $C_1$ through $C_{10}$ alkyl, or benzyl; $R_3$ is N-heterocyclic, N-alkyl-heterocyclic or quaternized N-heterocyclic; and n is 2, 3, 4, or 5.

5 Claims, No Drawings

N-AMINOALKYL AMIDE INHIBITORS OF PROTEIN KINASE C

FIELD OF THE INVENTION

The present invention relates to the field of compounds having protein kinase C inhibitory activity. More particularly the present invention relates to N-aminoalkyl amides for inhibiting protein kinase C and for treatment of tumors, inflammatory diseases, and cardiovascular diseases.

BACKGROUND OF THE INVENTION

Protein kinase C (PKC) is a family of calcium stimulatable and phospholipid-dependent serine/threonine-specific protein kinases which play an important role in cellular growth control, regulation, and differentiation. Protein kinase C is also fundamental to the processes involved in tumorigenicity, since it is the major high-affinity receptor for several classes of tumor promoters as well as for endogenous cellular diacylglycerols. These tumor promoters also stimulate protein kinase C catalysis. Castagna et al. (1982) J. Biol. Chem. 257:7847 reported direct activation of protein kinase C by tumor-promoting phorbol esters. The mechanisms of protein kinase C action have been described in U.S. Pat. No. 4,816,450 issued Mar. 28, 1989 to Bell et al., the disclosures of which are specifically incorporated as if fully set forth herein. Protein kinase C is activated by diacylglycerol (DAG), a neutral lipid, and when activated will transfer the $\gamma$-phosphate of MgATP to a serine or threonine residue on a substrate protein.

Since the activation of protein kinase C has been implicated in several human disease processes, including cancer tumors, inflammation, and reperfusion injury, inhibition of protein kinase C should be of great therapeutic value in treating these conditions.

Protein kinase C inhibitors have been reported to potentiate the antitumor activity of cis-platin both in vitro and in vivo (Grunicke et al. (1989) Adv. Enzyme Regul. 28:201; and German Offenlegungsschrift DE 3827974). In addition, it has been suggested that protein kinase C would be a potential target for therapeutic design because of its central role in cell growth (Tritton, T. R. and Hickman, J. A. Cancer Cells 2:95-102 (1990)).

Protein kinase C inhibitors have been demonstrated to block platelet aggregation and release of neutrophil activating agents such as platelet activating factor (PAF)(Schachtele et al. (1988) Biochem. Biophy. Res. Commun. 151:542; Hannun et al. (1987) J. Biol. Chem. 262:13620; Yamada et al. (1988) Biochem. Pharmacol. 37:1161). Protein kinase C inhibitors have also been shown to inhibit neutrophil activation, and chemotactic migration (McIntyre et al. (1987) J. Biol Chem. 262:15730; Lambreth et al. (1988) J. Biol. Chem. 263:3818; Pittet et al. (1987) J. Biol. Chem. 262:10072; and Gaudry et al. (1988) Immunology 63:715), as neutrophil degranulation and release of proteolytic enzymes and reactive oxygen intermediates (Wilson et al. (1986) J. Biol. Chem. 261:12616; Fujita et al. (1986) Biochem. Pharmacol. 35:4555; Berkow et al. (1987) J. Leukoc., Biol. 41:441; Salzer et al. (1987) Biochem. Biophys. Res. Commun. 148:747; Kramer et al. (1989) J. Biol. Chem. 262:5876; and Dewald et al. (1989) Biochem. J. 264:879). Thus inhibitors of protein kinase C have the capability of blocking all three of the most significant mechanisms of pathogenesis associated with myocardial reperfusion injury, and should thus have a decided therapeutic advantage. Additionally, the inhibitory effect of protein kinase C inhibitors on keratinocytes, and on the oxidative burst in neutrophils will lead to an anti-inflammatory effect.

N-[3-(dimethylamino)propyl] alkylamides have been reported as components in hairspray, hair conditioner, asphalt, emulsifiers, bactericides, waterproofing materials and stabilizers (GB 2220216 A1; U.S. Pat. No. 4,874,604; JP 01103663 A2; De Groot et al. (1988) Contact Dermatitis 19(4):289; Khim-Farm. Zh. 15(2) 28, 1981, JP 53035915, DE 2646199, Seifen, Oele, Fette, Wachse, 102 (7) 181, 1976, DE 2249471, JP 47042486 and EPO 402, 266).

Since the activation of protein kinase C has been implicated in several human disease processes, including cancer tumors, inflammation, and reperfusion injury, inhibition of protein kinase C should be of great value in treating these conditions. Consequently there is a need for novel protein kinase C inhibitors. Further, protein kinase C inhibitors that are relatively specific for inhibition of protein kinase C and which have minimal effects on other metabolic pathways such as those associated with stimulation of protein kinase C by cAMP are greatly desired. Inflammation and reperfusion injury, particularly pertaining to cardiac injury, are common conditions for which there exists no definitive treatment despite extensive research and appropriate treatments for these conditions are needed.

SUMMARY OF THE INVENTION

The present invention provides N-aminoalkyl amide compounds having the formula

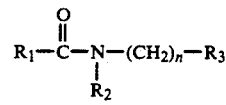

wherein $R_1$ is $C_8$ through $C_{15}$ alkyl; $R_2$ is H, $C_1$ through $C_{10}$ alkyl, or benzyl; $R_3$ is N-heterocyclic, N-alkylheterocyclic or quaternized N-heterocyclic; and n is 2, 3, 4, or 5.

The present invention also provides N-aminoalkyl amide compounds having the formula

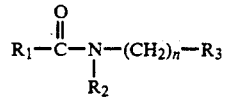

wherein $R_1$ is $C_1$ through $C_3$ alkyl; $R_2$ is $C_8$ through $C_{15}$ alkyl; $R_3$ is N-heterocyclic, N-alkylheterocyclic or $NR_4R_5$; $R_4$ and $R_5$ are independently $C_1$ through $C_{10}$ alkyl; and n is 2, 3, 4, or 5.

The present invention further provides pharmaceutical compositions comprising a pharmaceutically acceptable carrier or diluent and a compound having the formula

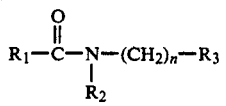

wherein $R_1$ is $C_8$ through $C_{15}$ alkyl; $R_2$ is H $C_1$ through $C_{10}$ alkyl, or benzyl; $R_3$ is N-heterocyclic, N-alkylheterocyclic, quaternized N-heterocyclic, $NR_4R_5$ or N$^+$R$_4$R$_5$R$_6$X$^-$; R$_4$, R$_5$ and R$_6$ are independently C$_1$ through C$_{10}$ alkyl; n is 2, 3, 4, or 5; and X is an anion, and pharmaceutical compositions comprising a pharmaceutically acceptable carrier or diluent and a compound having the formula

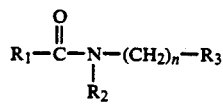

wherein R$_1$ is C$_1$ through C$_3$ alkyl; R$_2$ is C$_8$ through C$_{15}$ alkyl; R$_3$ is N-heterocyclic, N-alkylheterocyclic, quaternized N-heterocyclic, NR$_4$R$_5$ or N$^+$R$_4$R$_5$R$_6$X$^-$; R$_4$, R$_5$ and R$_6$ are independently C$_1$ through C$_{10}$ alkyl; n is 2, 3, 4, or 5; and X is an anion.

Another aspect of the present invention provides methods of inhibiting protein kinase C which comprises contacting protein kinase C with an inhibitory amount of a compound having the formula

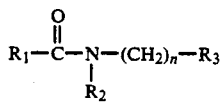

wherein R$_1$ is C$_8$ through C$_{15}$ alkyl; R$_2$ is H C$_1$ through C$_{10}$ alkyl, or benzyl; R$_3$ is N-heterocyclic, N-alkylheterocyclic, quaternized N-heterocyclic, NR$_4$R$_5$ or N$^+$R$_4$R$_5$R$_6$X$^-$; R$_4$, R$_5$ and R$_6$ are independently C$_1$ through C$_{10}$ alkyl; n is 2, 3, 4, or 5; and X is an anion.

The compounds useful for inhibiting protein kinase C are further useful for treating conditions related to, of affected by inhibition of protein kinase C, particularly cancer tumors, inflammatory disease, myocardial reperfusion injury, and cardiac dysfunctions related to reperfusion injury. Inhibition of protein kinase C can lead to inhibition of growth of cell and can thereby produce an anti-tumor effect. Further, inhibition of protein kinase C can also lead to inhibition of the oxidative burst in neutrophils, platelet aggregation, and keratinocyte proliferation, whereby an anti-inflammatory effect is achieved. The inhibitory activities of the compounds of the invention against platelet aggregation, neutrophil activation, and neutrophil release demonstrate their usefulness in treating reperfusion injury, particularly myocardial reperfusion injury.

The compounds useful for inhibiting protein kinase C are able to inhibit proliferation of tumor cells at low concentrations which should lessen the potential for deleterious side effects when the compounds of the invention are administered for treatment of tumors. The compounds inhibit protein kinase C at levels significantly less than those needed to inhibit protein kinase and should consequently have minimal effect on the metabolic pathways associated with stimulation of protein kinase by cAMP.

This invention is more particularly pointed out in the appended claims and is described in its preferred embodiments in the following description.

DETAILED DESCRIPTION OF THE INVENTION

The present invention provides novel N-aminoalkyl amides having the Formula I

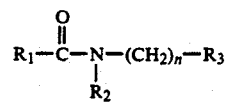

wherein R$_1$ is preferably C$_8$ through C$_{15}$ alkyl; R$_2$ is preferably H, C$_1$ through C$_{10}$ alkyl, or benzyl; R$_3$ preferably is N-heterocyclic, N-alkylheterocyclic or quaternized N-heterocyclic; and n is preferably 2, 3, 4, or 5. More preferably R$_1$ is C$_{12}$ through C$_{15}$ alkyl; R$_2$ is H, C$_1$ through C$_5$ alkyl, or benzyl; R$_3$ is N-heterocyclic, N-alkylheterocyclic or quaternized N-heterocyclic; and n is 2, 3, 4, or 5. Most preferably R$_1$ is C$_{12}$ through C$_{15}$ alkyl; R$_2$ is H, methyl, ethyl, propyl, or benzyl; R$_3$ is N-methyl morpholino; and n is 2 or 3.

Another aspect of the present invention provides N-aminoalkyl amide compounds having Formula I

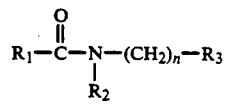

wherein R$_1$ is preferably C$_1$ through C$_3$ alkyl; R$_2$ is preferably C$_8$ through C$_{15}$ alkyl; R$_3$ is preferably N-heterocyclic, N-alkylheterocyclic, or NR$_4$R$_5$; R$_4$ and R$_5$ are preferably independently C$_1$ through C$_{10}$ alkyl; and n is preferably 2, 3, 4, or 5. More preferably R$_1$ is methyl; R$_2$ is C$_{16}$ alkyl; R$_3$ is N-methyl morpholino, pipecolino, or NR$_4$R$_5$; R$_4$ and R$_5$ are methyl or ethyl; and n is 2 or 3.

The present invention provides pharmaceutical compositions comprising a pharmaceutically acceptable carrier or diluent and a compound having the formula

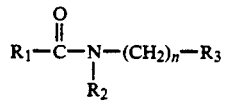

wherein R$_1$ is preferably C$_8$ through C$_{15}$ alkyl; R$_2$ is preferably H C$_1$ through C$_{10}$ alkyl, or benzyl; R$_3$ is preferably N-heterocyclic, N-alkylheterocyclic, quaternized N-heterocyclic, NR$_4$R$_5$ or N$^+$R$_4$R$_5$R$_6$X$^-$; R$_4$, R$_5$ and R$_6$ are preferably independently C$_1$ through C$_{10}$ alkyl; n is preferably 2, 3, 4, or 5; and X is an anion. More preferably R$_1$ is C$_{12}$ through C$_{15}$ alkyl; R$_2$ is H, C$_1$ through C$_5$ alkyl, or benzyl; R$_3$ is N-heterocyclic, N-alkylheterocyclic or quaternized N-heterocyclic, NR$_4$R$_5$ or N$^+$R$_4$R$_5$R$_6$X$^-$; R$_4$; R$_5$ and R$_6$ are independently C$_1$ through C$_{10}$ alkyl; n is 2, 3, 4, or 5; and X is an anion. Most preferably R$_1$ is C$_{12}$ through C$_{15}$ alkyl; R$_2$ is H, methyl, ethyl, propyl or benzyl; R$_3$ is N-methylmorpholino, or NR$_4$R$_5$; R$_4$ and R$_5$ are independently methyl or ethyl; and n is 2 or 3.

The present invention also provides pharmacuetical compositions comprising a pharmaceutically acceptable carrier or diluent and a compound having the formula

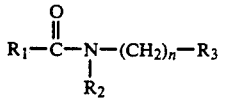

wherein R$_1$ is preferably C$_1$ through C$_3$ alkyl; R$_2$ is preferably C$_8$ through C$_{15}$ alkyl; R$_3$ is preferably N- heterocyclic, N-alkylheterocyclic, quaternized N-heterocyclic, $NR_4R_5$ or $N^+R_4R_5R_6X^-$; $R_4$, $R_5$ and $R_6$ are preferably independently $C_1$ through $C_{10}$ alkyl; n is 2, 3, 4, or 5; and X is an anion. More preferably $R_1$ is methyl; $R_2$ is $C_{16}$ alkyl; $R_3$ is N-methyl morpholino, or $NR_4R_5$; $R_4$ and $R_5$ are methyl or ethyl; n is 2 or 3. When $R_6$ is methyl, X is preferably $I^-$.

As used herein, alkyl substituents include straight chain, branched and cyclic moieties, preferably straight chain species. N-heterocyclic refers to substituted or unsubstituted nitrogen-containing cyclic moieties. The nitrogen heterocycles are attached to the alkyl chain via nitrogen in the heterocyclic ring. Suitable nitrogen heterocycles are preferably five or six membered rings which may be saturated or unsaturated, and may optionally contain other heteroatoms such as oxygen, sulfur or further nitrogen. Preferred substituents for the nitrogen heterocycles include lower alkyl, such as methyl, ethyl or propyl, or hydroxyl. Preferred nitrogen heterocycles include piperidino, substituted piperidino such as pipecolino, or morpholino. N-alkyl heterocyclic refers to N-alkyl substituted nitrogenous heterocyclic moieties as described herein. The N-alkyl substituent is preferably $C_1$ to $C_5$ alkyl, more preferably methyl. Suitable N-alkyl heterocycles include N-methyl morpholino, N-methyl piperidino, and N-methyl imidazolino. Quaternized N-heterocyclic refers to nitrogenous heterocyclic moieties as defined herein containing quaternized nitrogen, preferably at the point of attachment.

Salts and bases of the compounds are also within the scope of the invention, particularly the quaternary nitrogen salts. Suitable salts include halide, acetate, succinate, maleate, fumarate, methylsulfonate, sulfonate and species containing metallic and other carbanion counterions such as sodium, potassium, magnesium and zinc.

A further aspect of the invention provides methods of inhibiting protein kinase C which comprise contacting protein kinase C, or cells, tissues or cell cultures containing protein kinase C, with an inhibitory amount of a compound having the formula

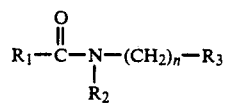

wherein $R_1$ is preferably $C_8$ through $C_{15}$ alkyl; $R_2$ is preferably H, $C_1$ through $C_{10}$ alkyl, or benzyl; $R_3$ is preferably N-heterocyclic, N-alkylheterocyclic, quaternized N-heterocyclic, $NR_4R_5$ or $N^+R_4R_5R_6X^-$; $R_4$, $R_5$ and $R_6$ are preferably independently $C_1$ through $C_{10}$ alkyl; n is preferably 2, 3, 4, or 5; and X is an anion. More preferably $R_1$ is $C_{12}$ through $C_{15}$ alkyl; $R_2$ is H, $C_1$ through $C_5$ alkyl, or benzyl; $R_3$ is N-heterocyclic, N-alkylheterocyclic or quaternized N-heterocyclic, $NR_4R_5$ or $N^+R_4R_5R_6X^-$; $R_4$, $R_5$ and $R_6$ are independently $C_1$ through $C_{10}$ alkyl; n is 2, 3, 4, or 5; and X is an anion. Most preferably $R_1$ is $C_{12}$ through $C_{15}$ alkyl; $R_2$ is H, methyl, ethyl, propyl or benzyl; $R_3$ is N-methylmorpholino, or $NR_4R_5$; $R_4$ and $R_5$ are independently methyl or ethyl; and n is 2 or 3.

The present invention also provides methods of inhibiting protein kinase C which comprise contacting protein kinase C with an inhibitory amount of a compound having the formula

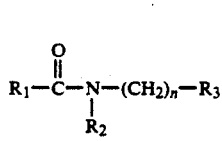

wherein $R_1$ is preferably $C_1$ through $C_3$ alkyl; $R_2$ is preferably $C_8$ through $C_{15}$ alkyl; $R_3$ is preferably N-heterocyclic, N-alkylheterocyclic, quaternized N-heterocyclic, $NR_4R_5$ or $N^+R_4R_5R_6X^-$; $R_4$, $R_5$ and $R_6$ are preferably independently $C_1$ through $C_{10}$ alkyl; n is 2, 3, 4, or 5; and X is an anion. More preferably $R_1$ is methyl; $R_2$ is $C_{16}$ alkyl; $R_3$ is N-methyl morpholino, or $NR_4R_5$; $R_4$ and $R_5$ are methyl or ethyl; n is 2 or 3.

The compounds useful for inhibiting protein kinase C are further useful for treating conditions related to, or affected by inhibition of protein kinase C, particularly cancer tumors, inflammatory disease, reperfusion injury, and cardiac dysfunctions related to reperfusion injury.

Accordingly, the present invention provides methods of inhibiting an oxidative burst in neutrophils which comprise contacting a neutrophil with a protein kinase C inhibitory concentration of an N-aminoalkyl amide compound capable of inhibiting protein kinase C as defined hereinabove, or contacting the neutrophil with an amount of such compound effective to inhibit the oxidative outburst.

The invention further provides methods for treating inflammation which comprise administering to a mammal suffering from inflammation a protein kinase C inhibitory concentration of an N-aminoalkyl amide compound capable of inhibiting protein kinase C as defined hereinabove, or administering to the mammal an amount of such compound effective to inhibit inflammation.

The invention additionally provides methods for inhibiting growth of mammalian tumor cells which comprises contacting a mammalian tumor cell with a protein kinase C inhibitory amount of an N-aminoalkyl amide compound capable of inhibiting protein kinase C as defined hereinabove, or contacting the tumor cell with an amount of such compound effective to inhibit growth of the tumor cell.

A further embodiment of the invention provides methods for treating mammalian tumors which comprise administering to a mammal having a tumor a protein kinase C inhibitory concentration of an N-aminoalkyl amide compound capable of inhibiting protein kinase C as defined hereinabove, or administering to the mammal having a tumor an amount of such compound effective to inhibit growth of the tumor.

An additional embodiment of the invention provides methods of inhibiting mammalian keratinocyte proliferation which comprises administering to a mammalian keratinocyte a protein kinase C inhibitory amount of an N-aminoalkyl amide compound capable of inhibiting protein kinase C as defined hereinabove, or administering to the keratinocyte an amount of such compound effective to inhibit proliferation of the keratinocyte.

Cancer is a disease characterized in part by uncontrolled cell growth. Protein kinase C is directly involved in cellular growth control and is believed to be involved in tumor formation. Protein kinase C is the major, if not exclusive, intracellular receptor of phorbol esters which are very potent tumor promoters. Phorbol esters and other tumor promoters bind to and activate protein kinase C. Since diacylglycerol (DAG) and phorbol esters interact at the same site, DAG's have been suggested to be the "endogenous phorbol esters" by analogy with the opiate receptor where the conservation of a high affinity receptor implied the existence of an endogenous analogue. DAG has been shown to increase the affinity of protein kinase C for $Ca^{+2}$ and phospholipid and thus activates protein kinase C at cellular levels of these essential cofactors. Extracellular signals including hormones, growth factors, and neurotransmitters are known to stimulate phosphatidylinositol turnover resulting in the generation of $IP_3$ and DAG. Structures of 40 distinct oncogenes of viral and cellular origin have revealed that oncogenes encode altered forms of normal cellular proteins. Several of the gene products appear related to growth factors or other elements involved in transmembrane signalling. These oncogene products appear to function by altering the level of critical second messengers. Cells transformed with the oncogenes ras, sis, erbB, abl, and src have been shown to contain elevated levels of DAG which is then believed to activate protein kinase C. Indeed studies on ras transformed cells have shown protein kinase C activation to concomitant with elevation of DAG.

Phorbol esters, such as phorbol myristate acetate (PMA), have complex effects on cells including effects on membrane function, mitogenesis, differentiation, and gene expression. Synthetic diacylglycerols mimic many of the effects of PMA in vitro and inhibitors of protein kinase C have been shown to block PMA-induced effects on cells. Thus, protein kinase C may mediate the actions of certain oncogenes, such as ras, which cause intracellular increases in DAG and concomitant increases in protein kinase C. In addition, activation of protein kinase C leads to the expression of c-myc, c-fos, c-cis, c-fms, nuclear protooncogenes important in cell transformation. Overexpression of protein kinase C in NIH 3T3 cells causes altered growth regulation and enhanced tumorigenicity and in rat fibroblasts leads to anchorage-independent growth in soft agar. In these experiments, overexpression of protein kinase C in these cells resulted in tumor formation in animals receiving transplanted cells.

Several studies have shown increased expression of protein kinase C in certain tumor types such as breast and lung carcinomas. Activated protein kinase C has also been detected in human colon carcinomas although increased expression on the gene level was not seen. Topoisomerases are directly modulated by protein kinase C as substrates for the enzyme and protein kinase C inhibitors have been shown to potentiate the action of chemotherapy drugs such as cis-platinum.

New and more potent compounds which have been identified specifically as inhibitors of protein kinase C are showing early promise as therapeutic agents in inhibiting tumor growth in animal models.

Animal studies have shown that perhaps 50% or more of ischemic-related myocardial damages can be attributed to polymorphonuclear leukocytes (neutrophils) which accumulate at the site of occlusion. Damage from the accumulated neutrophils may be due to the release of proteolytic enzymes from the activated neutrophils or the release of reactive oxygen intermediates (ROI). Much of the "no reflow" phenomenon associated with myocardial ischemia is attributed to myocardial capillary plugging. The plugging of capillaries has been attributed to both aggregated platelets and aggregated neutrophils. Although both cell types are aggregated during the ischemic event, the relative contribution of each to capillary plugging has not yet been established. It is well accepted that the damage by neutrophils to myocardial tissue proceeds through a cascade of events, one of the earliest being the bonding of activated neutrophils to damaged vascular endothelium. However, the binding of the neutrophils is significantly enhanced by their activation and this an even earlier event is the generation of molecules (such as cytokines, and chemotactic factors) which can function as activation stimuli. These molecules probably originate from damaged and aggregated platelets, from damaged vascular endothelium, or from the oxidation of plasma proteins or lipids by endothelial-derived oxidants.

Strategies for overcoming the deleterious effects of reactive oxygen intermediates have centered in the development of scavengers for the molecules. Superoxide dismutase (SOD) has been shown to be a particularly effective scavenger of superoxide, but suffers from a very short half-life in the blood. Several companies have tackled this problem by creating versions of this enzyme with increased half-lives by techniques such as liposome encapsulation or polyethylene glycol conjugation. Reports on the effectiveness of these new version are mixed. Catalase, a scavenger of hydrogen peroxide, and hydroxyl radical scavengers have also been tested and found to be effective to varying degrees. However, none of the strategies designed to scavenge reactive oxygen intermediates will prevent the aggregation of platelets, the release of chemotactic molecules, the activation and adherence of neutrophils to vascular endothelium, or the release of proteolytic enzymes from activated neutrophils.

The advantage of protein kinase C inhibitors as therapeutics for reperfusion injury is that they have been demonstrated to 1) block platelet aggregation and release of neutrophil activating agents such as PAF, 2) block neutrophil activation, chemotactic migration, and adherence to activated or damaged endothelium, and 3) block neutrophil release of proteolytic enzymes and reactive oxygen intermediates. Thus these agents have the capability of blocking all three of the most significant mechanisms of pathogenesis associated with reperfusion injury and should thus have a decided therapeutic advantage.

Pharmaceutically acceptable salts of the compounds of the invention are also useful in the methods of the invention. Pharmaceutically acceptable salts useful in the invention include salts of hydrochloric acid, hydrobromic acid, fumaric acid, oxalic acid, malic acid, succinic acid, pamoic acid, sulfuric acid and phosphoric acid.

The compounds of the invention may be prepared by methods known in the art. Examples of methods of synthesizing the compounds are shown in Schemes 1 through 6.

As shown in Scheme 1, acylation of N,N-dimethyl-1,3-propanediamine (5) and N,N,N'-trimethyl-1,3-propanediamine (2) with palmitoyl chloride gave 6 and 4, respectively.

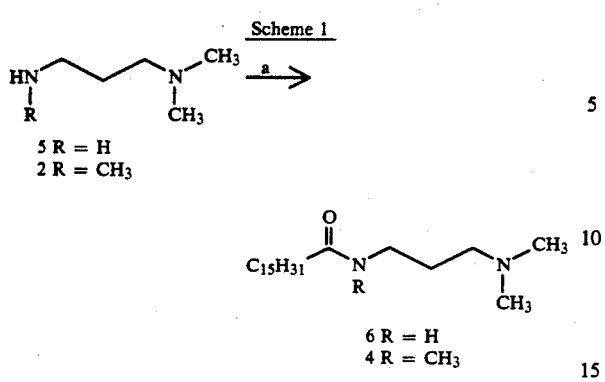

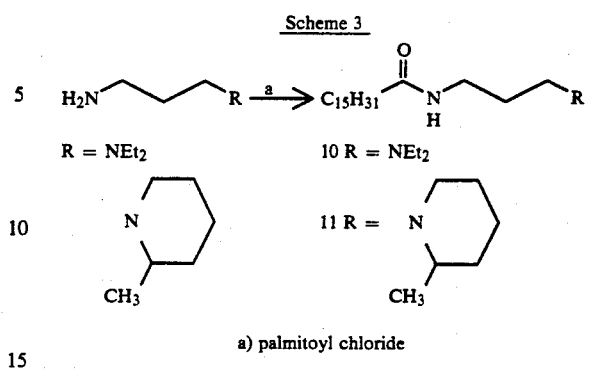

a) palmitoyl chloride

The N-ethyl and N-n-propyl analogs were prepared by acylation of 5 with acetic anhydride and propionyl chloride, respectively, followed by reduction with lithium aluminumhydride, as shown in Scheme 2. The resulting diamines were then acylated with palmitoyl chloride to give 7 and 8. The N-isopropyl amide (9) was prepared by imine formation of 5 with acetone followed by reduction with sodium borohydride.

Quaternary salt 15 was prepared upon treatment of 4, with methyl iodide, as shown in Scheme 4. Similarly treatment of 14 with excess methyl iodide gave 16.

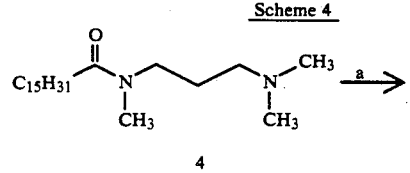

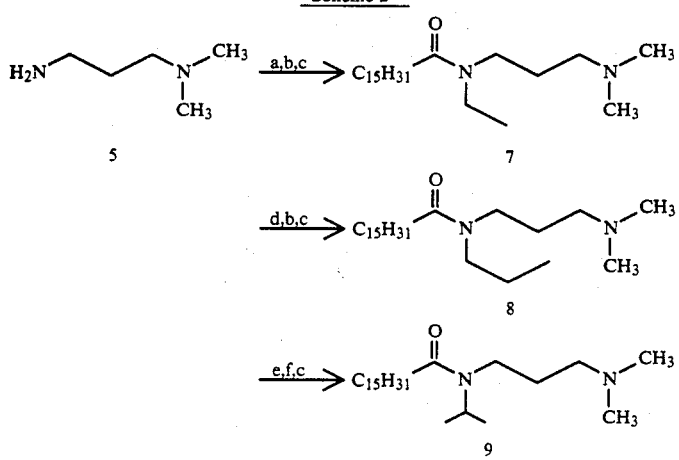

a) $Ac_2O$, Py, $CH_2Cl_2$; b) LAH, THF; c) $C_{15}H_{31}COCl$, $Et_2O$;
d) $C_2H_5COCl$, $CH_2Cl_2$; d) acetone; f) $NaBH_4$, MeOH.

As shown in Scheme 3, the amino moiety of the molecule was modified, by acylating the following commercially available amines: N,N-diethyl-1,3-propanediamine, 1-(3-aminopropyl)-2-pipecoline, 4-(3-aminopropyl)morpholine, with palmitoyl chloride to gave the corresponding amides 10, 11, and 14 respectively. The corresponding hydrochloride salts were also prepared and tested.

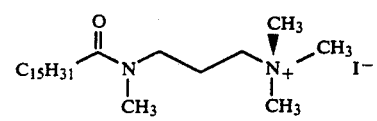

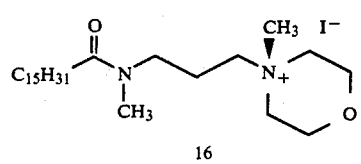

-continued
Scheme 4 a) CH₃I, Et₂O

Alternatively reductive amination of 4-(3-aminopropyl) morpholine with benzaldehyde/NaBH₄, followed by acylation with palmitoyl chloride gave 17, as shown in Scheme 5. Quaternaration with methyl iodide gave 18.

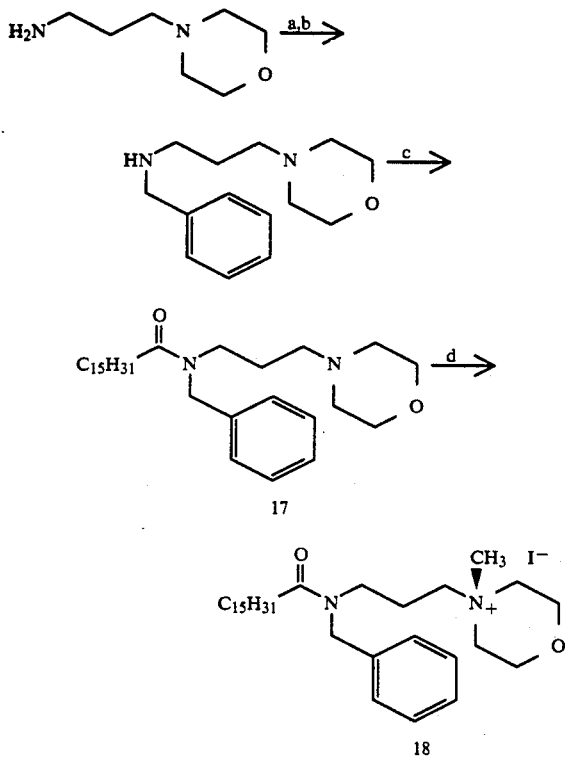

The carbonyl moiety was transposed from the long chain to the short chain by reducing 6 with lithium aluminumhydride, followed by acylation with acetic anhydride gave 20, as shown in Scheme 6.

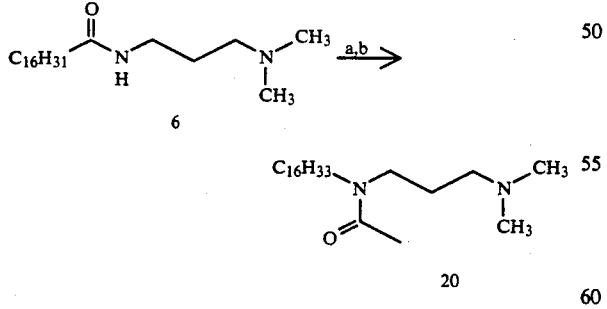

a) LAH, THF; b) Ac₂O, CH₂Cl₂

The compounds of the invention may be administered by any method that produces contact of the active ingredient with the agent's site of action in the body of a mammal including but not limited to oral, intravenous, and intraparenteral. The compounds of the invention may be administered singly, or in combination with other compounds of the invention, other pharmaceutical compounds, such as chemotherapy compounds, or other therapies, such as radiation treatment. The compounds are preferably administered with a pharmaceutically acceptable carrier selected on the basis of the selected route of administration and standard pharmaceutical practice.

The compounds of the invention are administered to mammals, preferably humans, in therapeutically effective amounts or concentrations which are effective to inhibit protein kinase C, or to inhibit tumor cell growth, inhibit inflammation of tissue, inhibit keratinocyte proliferation, inhibit oxidative burst from neutrophils or inhibit platelet aggregation. The dosage administered in any particular instance will depend upon factors such as the pharmacodynamic characteristics of the particular compound of the invention, and its mode and route of administration; age, health, and weight of the recipient; nature and extent of symptoms; kind of concurrent treatment, frequency of treatment, and the effect desired. It is contemplated that the daily dosage of the compounds will be in the range of from about 5 to about 400 mg per kg of body weight, preferably from about 10 to about 200 mg per kg body weight, and more preferably from about 10 to about 50 mg per kg per day, and preferably administered in divided doses 2 to 4 times a day or in sustained release form.

The compounds of the invention may be administered orally in solid dosage forms, such as capsules, tablets, and powders, or in liquid dosage forms, such as elixirs, syrups, and suspensions. They may also be administered parenterally in sterile liquid dosage forms.

The compounds of the invention may be formulated into dosage forms according to standard practices in the field of pharmaceutical preparations. See Remington's Pharmaceutical Sciences, A. Osol, Mack Publishing Company, Easton, Pa., a standard reference text in this field.

For example, the compounds of the invention may be mixed with powdered carriers, such as lactose, sucrose, mannitol, starch, cellulose derivatives, magnesium stearate, and stearic acid for insertion into gelatin capsules, or for forming into tablets. Both tablets and capsules may be manufactured as sustained release products for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration may contain coloring and flavoring to increase patient acceptance, in addition to a pharmaceutically acceptable diluent such as water, buffer or saline solution.

For parenteral administration, the compounds of the invention may be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of the compound of the invention. Stabilizing agents, antioxidizing agents and preservatives may also be added. Suitable antioxidizing agents include sodium bisulfite, sodium sulfite, and ascorbic acid, citric acid and its salts, and sodium EDTA. Suitable preservatives include benzalkonium chloride, methyl-or propyl-paraben, and chlorbutanol.

EXAMPLES

Example 1

N-Hexadecanoyl-3-trimethylammoniumpropylamine iodide (15)

A mixture of N,N-dimethyl-N'-hexadecanoyl-1,3-propanediamine (30.2 g, 88.8 mmole) and iodomethane (18.9 g, 133 mmole) in diethyl ether (350 mL) was stirred at room temperature. Chloroform (500 mL) was added and the reaction mixture stirred at room temperature for 1.5 hours. The reaction mixture was filtered. A second crop of crystals was recovered from the filtrate. The combined crops were dried in vacuo overnight to give the title compound (38.0 g, 88.7%) as a solid. mp. 118° C. $^1$H NMR (200 MHz, CDCl$_3$): $\delta$0.847 (3H, t, J=6.4 Hz), 1.250 (26H, bs), 1.57 to 1.64 (2H, m), 2.06 to 2.20 (2H, m), 2.30 (2H, t, J=7.6 Hz), 3.397 (9H, s), 3.79 to 3.88 (2H, m), and 7.174 (1H, t, J=5.7 Hz). Analysis calculated for $C_{22}H_{47}IN_2O$: C, 54.76 H, 9.82; N, 5.80. Found: C, 54.66; H, 9.76; N, 5.74.

EXAMPLE 2

2-Methyl-1-[3-(N-hexadecanoyl)aminopropyl]piperidine (11)

To a solution of 1-(3-aminopropyl)-2-pipecoline (1.00 g, 6.40 mmole) in methylene chloride (25 mL) was added palmitoyl chloride (1.73 g, 6.40 mmole) in small portions. The reaction mixture was stirred at room temperature overnight. The reaction mixture was washed twice with saturated aqueous sodium bicarbonate and once with brine. The organic layer was dried over magnesium sulfate and the salts removed by filtration. The solvent was removed under reduced pressure and the residue dried in vacuo to give the title compound (2.12 g, 83%), mp. 48°-50° C. $^1$H NMR (300 MHz, CDCl$_3$): $\delta$0.883 (3H, t, J=6.5 Hz), 1.136 (3H, d, J=5.5 Hz), 1.254 (24H, bs), 1.60 to 1.70 (4H, m), 2.157 (2H, t, J=7.6 Hz), 2.37 to 2.39 (2H, m), 2.89 to 2.94 (3H, m), 3.24 to 3.27 (1H, m), 3.40 to 3.44 (1H, m), and 7.266 (1H, bs). Analysis calculated for $C_{25}H_{50}N_2O.\frac{1}{4}H_2O$ C, 75.16; H, 12.61; N, 7.01. Found: C, 75.16; H, 12.69; N, 7.16.

EXAMPLE 3

2-Methyl-1-[3-(N-hexadecanoyl)aminopropyl]piperidine hydrochloride (11, hydrochloride salt)

To a solution of 2-methyl-1-[3-(N-hexadecanoyl)aminopropyl]piperidine (0.47 g, 1.2 mmole) in diethyl ether was added an ethereal solution of hydrogen chloride. The reaction mixture was placed in the refrigerator overnight. The precipitate was filtered. The gummy paste was dissolved in methanol and the solvent removed under reduced pressure to give the title compound (0.37 g, 71%) as a pale paste. $^1$H NMR (300 MHz, CDCl$_3$): mixture of rotamers, major peaks given. $\delta$0.870 (H, t, J=6.7 Hz), 1.243 (24H, bs), 1.533 (3H, d, J=6.4 Hz), 1.59 to 1.66 (2H, m), 1.81 to 1.88 (2H, m), 2.06 to 2.70 (8H, m), 2.74 to 3.10 (2H, m), 3.12 to 3.70 (3H, m), and 7.264 (1H, bs). IR (neat): 2686, 1941, 1649, 1549, 1468, 1379, 1230, and 1123 cm$^{-1}$. Analysis calculated for $C_{25}H_{51}ClN_2O.\frac{3}{4}H_2O$: C, 67.53; H, 11.90; N, 6.30; Cl, 7.97. Found: C, 67.55; H, 11.85; N, 6.29; Cl, 8.04.

EXAMPLE 4

N,N-Diethyl-N'-hexadecanoyl-1,3-propanediamine (10)

To a solution of 3-diethylaminopropylamine (4.13 g, 31.7 mmole) in methylene chloride (50 mL) was added palmitoyl chloride (9.15 g, 33.3 mmole) in small portions. The reaction mixture was stirred at room temperature overnight. The solvent was removed under reduced pressure. The residue was dissolved in 1N aqueous sodium hydroxide (90 mL), chloroform (100 mL) and methanol (200 mL). The solution was transferred to a separatory funnel then chloroform (100 mL) and 1N aqueous sodium hydroxide (100 mL) was added and the layers separated. The aqueous layer was extracted twice with chloroform (100 mL portions). The solution was transferred to a separatory funnel then chloroform. The organic layer was dried over magnesium sulfate and the salts removed by filtration. The solvent was removed under reduced pressure to give the title compound (11.6 g, 100%) as a gum. $^1$H NMR (300 MHz, CDCl$_3$): $\delta$0.881 (3H, t, J=6.6 Hz), 1.053 (6H, t, J=7.1 Hz), 1.252 (24H, bs), 1.56 to 1.67 (2H, m), 2.129 (2H, t, J=7.7 Hz), 2.50 to 2.57 (6H, m), 3.31 to 3.37 (2H, m), and 7.392 (1H, bs). IR (neat): 3307, 3219, 3152, 3085, 2949, 2920, 2850, 1734, 1642, 1082 cm$^{-1}$. Analysis calculated for $C_{23}H_{48}N_2O.\frac{3}{4}H_2O$: C, 74.94; H, 13.12; N, 7.59. Found: C, 74.68; H, 13.11; N, 7.52.

EXAMPLE 5

N,N-Diethyl-N'-hexadecanoyl-1,3-propanediamine hydrochloride (10, hydrochloride salt)

To a solution of N,N-diethyl-N'-hexadecanoyl-1,3-propanediamine (10.9 g, 29.6 mmole) in diethyl ether was added an ethereal solution of hydrogen chloride. The reaction mixture was placed in the refrigerator overnight. The precipitate was filtered to give the title compound (8.60 g, 65%) as a pasty solid. 1H NMR (300 MHz, CDCl$_3$): $\delta$0.855 (3H, t, J=6.7 Hz), 1.229 (24H, bs), 1.367 (3H, bs), 1.626 (2H, bs), 2.08 to 2.10 (2H, m), 3.153 (6H, bs), 3.414 (2H, bs), and 6 32 to 6.36 (1H, bs). Analysis calculated for $C_{23}H_{46}N_2O.1.4$ HCl.1.5 $H_2O$: C, 62.12; H, 11.42; N, 6.29; Cl, 11.16. Found: C, 62.50; H, 11.52; N, 6.31; Cl, 11.28.

EXAMPLE 6

N,N-Dimethyl-N'-ethyl-N'-hexadecanoyl-1,3-propanediamine (7)

To a solution of N,N-dimethyl-N'-ethyl-1,3-propanediamine (1.18 g, 9.06 mmole) in methylene chloride (20 mL) was added palmitoyl chloride (2.20 g, 8.00 mmole) dropwise. The reaction mixture was stirred at room temperature overnight.

The solvent was removed under reduced pressure. The residue was taken up in methanol (40 mL), chloroform (20 mL), and 1N aqueous sodium hydroxide (18 mL) and transferred to a separatory funnel. To the solution was added chloroform (20 mL) and water (20 mL). The layers were separated and the aqueous layer washed twice with chloroform (20 mL portions). The combined organic layer was dried over magnesium sulfate and the salts removed by filtration. The solvent was removed under reduced pressure and the residue chromatographed on silica (230 to 400 mesh) with chloroform (100%) to chloroform:methanol (4:1) to give the title compound (0.85 g, 29%) as an oil. $^1$H NMR (300 MHz, CDCl$_3$): mixture of rotamers, $\delta$0.881 (3H, t, J=6.7 Hz), 1.104 and 1.167 (3H, t, J=7.1 Hz), 1.255 (26H, bs), 1.60 to 1.77 (4H, m), 1.965 (2H, bs), 2.22 to 2.35 (10H, m), and 3.26 to 3.41 (4H, m). IR (neat): 2924, 2854, 1645, 1463, and 1425 cm$^{-1}$. Analysis calculated for $C_{23}H_{48}N_2O.\frac{3}{4}H_2O$: C, 72.29; H, 13.06; N, 7.33. Found: C, 72.20; H, 12.74; N, 7.36.

EXAMPLE 7

N,N-Dimethyl-N'-ethyl-N'-hexadecanoyl-1,3-propanediamine hydrochloride (7, hydrochloride salt)

Hydrogen chloride gas was bubbled into a solution of N,N-dimethyl-N'-ethyl-N'-hexadecanoyl-1,3-propanediamine (0.64 g, 1.7 mmole) in methanol (20 mL). The solvent was removed under reduced pressure and the residue titurated with diethyl ether to yield the title compound (0.67 g, 96%) as a white solid. mp 81°-83 ° C. $^1$H NMR (300 MHz, CD$_3$OD): δ0.691 (3H, t, J=6.7 Hz), 1.012 (3H, t, J=7.1 Hz), 1.081 (24H, bs), 1.75 to 1.82 (2H, m), 2.207 (2H, t, J=7.1 Hz), 2.679 (6H, s), 2.879 (2H, t, J=7.1 Hz), and 3.19 to 3.25 (4H, m). IR (KBr): 2957, 1913, 1653, and 1251 cm$^{-1}$. Analysis calculated for $C_{23}H_{49}ClN_2O.\frac{1}{4}H_2O$: C, 67.41; H, 12.18; N, 6.84; Cl, 8.66. Found: C, 67.46; H, 12.14; N, 6.85; Cl, 8.71.

EXAMPLE 8

N,N-Dimethyl-N'-(2-propyl)-N'-hexadecanoyl-1,3-propanediamine (9)

To a solution of N,N-dimethyl-N'-(2-propyl)-1,3-propanediamine (1.0 g, 6.9 mmole) dropwise. The reaction mixture was stirred at room temperature overnight. The solvent was removed under reduced pressure and the residue dissolved in 1N aqueous sodium hydroxide (18 mL), chloroform (20 mL), and methanol (40 mL). The solution was transferred to a separatory funnel and to the solution was added chloroform (20 mL) and water (30 mL). The layers were separated and the aqueous layer extracted twice with chloroform (20 mL portions). The combined organic layer was dried over magnesium sulfate and the salts removed by filtration. The solvent was removed under reduced pressure and the residue purified by flash column chromatography on silica (230 to 400 mesh) with chloroform:methanol (185:15) to give the title compound (0.88 g, 33%) as an oil. $^1$H NMR (300 MHz, CDCl$_3$): mixture of rotamers. δ0.873 (3H, t, J=6.6 Hz), 1.130 and 1.183 (6H, d, J=6.7 Hz), 1.247 (24H, bs), 1.58 to 1.75 (4H, m), 2.231 and 2.273 (6H, s), 2.30 to 2.40 (4H, m), 3.15 to 3.21 (2H, m), and 4.00 to 4.10 (1H, septet, major rotamer). IR (neat): 2923, 2815, 1644, and 1098 cm$^{-1}$. Analysis calculated for $C_{24}H_{50}N_2O$: C, 75.33; H, 13.17; N, 7.32. Found: C, 75.06; H, 13.14; N, 7.29.

EXAMPLE 9

N,N-Dimethyl-N'-(2-propyl)-N'-hexadecanoyl-1,3-propanediamine hydrochloride (9, hydrochloride salt)

To a solution of N,N-dimethyl-N'-(2-propyl)-N'-hexadecanoyl-1,3-propanediamine (0.20 g, 0.52 mmole) in diethyl ether was added an ethereal solution of hydrogen chloride. The reaction mixture was placed in the refrigerator overnight. The title compound (0.09 g, 45%) was collected by filtration as a white solid. mp 80°-82° C. $^1$H NMR (300 MHz, CD$_3$OD): δ0.65 to 0.69 (3H, bs), 1.080 (24H, bs), 11.37 to 1.40 (2H, m), 1.71 to 1.75 (2H, m), 2.21 to 2.24 (2H, m), 2.64 to 2.68 (6H, bs), 2.86 to 2.90 (2H, m), 3.06 to 3.10 (6H, bs), and 3.90 to 4.10 (1H, m). IR (KBr): 2915, 2848, 1649, and 1203 cm$^{-1}$. Analysis calculated for $C_{24}H_{51}ClN_2O.\frac{1}{4}H_2O$: C, 68.05; H, 12.25; N, 6.61; Cl, 8.37. Found: C, 67.86; H, 12.11; N, 6.57; Cl, 8.24.

EXAMPLE 10

N,N-Dimethyl-N'-hexadecanoyl-N'-propyl-1,3-propanediamine(8)

To a solution of N,N-diethyl-N'-propyl-1,3-propanediamine (2.80 g, 19.6 mmole) in methylene chloride (50 mL) was added palmitoyl chloride (5.66 g, 20.6 mmole). The reaction mixture was stirred at room temperature overnight. The solvent was removed under reduced pressure. The residue was dissolved in 1N aqueous sodium hydroxide (27 mL), chloroform (30 mL), and methanol (60 mL). The solution was transferred to a separatory funnel and to the solution was added chloroform (30 mL) and 1N aqueous sodium hydroxide (30 mL). The layers were separated and the aqueous layer extracted twice with chloroform (30 mL portions). The combined organic layer was dried over magnesium sulfate and the salts removed by filtration. The solvent was removed under reduced pressure to give the title compound (3.20 g, 38%) as an oil. $^1$H NMR (300 MHz, CDCl$_3$): δ0.82 to 0.95 (6H, m), 1.26 (24H, bs), 1.50 to 1.80 (6H, m), 2.20 to 2.40 (10H, m), and 3.16 to 3.38 (4H). IR (neat): 2920, 2851, 1648, and 1027 cm$^{-1}$. Analysis calculated for $C_{24}H_{50}N_2O.H_2O$: C, 71.94; H, 13.08; N, 6.99. Found: C, 71.86; H, 12.64; N, 6.70.

EXAMPLE 11

N,N-Dimethyl-N'-hexadecanoyl-N'-propyl-1,3-propanediamine hydrochloride (8, hydrochloride salt)

To a solution of N,N-dimethyl-N'-hexadecanoyl-N'-propyl-1,3-propanediamine (2.78 g, 6.94 mmole) in diethyl ether was added an ethereal solution of hydrogen chloride. The reaction mixture was placed in the refrigerator overnight. The precipitate was filtered to give the title compound (2.01g, 63%) as a paste. $^1$H NMR (300 MHz, CDCl$_3$): δ0.83 to 0.93 (6H, m), 1.232 (24H, bs), 1.54 to 1.69 (4H, m), 2.00 to 2.20 (2H, m), 2.288 (2H, t, J=7.5 Hz), 2.788 (3H, s), 2.803 (3H, s), 2.95 to 3.10 (2H, m), 3.225 (2H, t, J=7.7 Hz), and 3.401 (2H, t, J=6.7 Hz). IR (neat): 2917, 2848, 1633, and 1172 cm$^{-1}$. Analysis calculated for $C_{24}H_{50}N_2O.\frac{3}{4}HCl.1.2H_2O$: C, 65.52; H, 12.07; N, 6.36; Cl, 9.67. Found: C, 65.51; H, 11.98; N, 6.36; Cl, 9.73.

EXAMPLE 12

4-[N-hexadecanoyl-N-methyl-4-(3-aminopropyl)]-4-methylmorpholimium iodide (16)

To a solution of N-hexadecanoyl-4-(3-aminopropyl)-morpholine (0.50 g, 1.3 mmole) in diethyl ether was added excess iodomethane. The reaction mixture was stirred at room temperature overnight. The precipitate was filtered and crystallized from ethyl acetate to give the title compound (0.26 g, 37%) as a white solid. mp. 95°-96° C. $^1$H NMR (300 MHz, CDCl$_3$): δ0.879 (3H, t, J=6.6 Hz), 1.247 (24H, bs) 1.50 to 1.65 (2H, m), 2.08 to 2.23 (2H, m) 2.311 (2H, t, J=7.6 Hz), 3.42 to 3.50 (2H, m), 3.446 (2H, s) 3.58 to 3.72 (4H, m) and 3.95 to 4.15 (6H, m). IR (neat): 2919, 2850, 1647, and 1127 cm$^{-1}$. Analysis calculated for $C_{25}H_{51}IN_2O_2.\frac{1}{4}H_2O$: C, 55.28; H, 9.56; N, 5.16. Found: C, 55.24; H, 9.34; N, 5.18.

EXAMPLE 13

N-Acetyl-N-hexadecyl-N',N'-dimethyl-1,3-propanediamine (20)

A solution of N,N-dimethyl-N'-hexadecanoyl-1,3-propanediamine (0.54 g, 1.6 mmole) in tetrahydrofuran (15 mL) was added to a solution of 1M lithium aluminumhydride (3.0 mL) in tetrahydrofuran (10 mL) dropwise. The reaction mixture was refluxed for 8 hours then cooled to room temperature. The reaction mixture was quenched sequentially and slowly with water (10 drops), 15% aqueous sodium hydroxide (10 drops) and water (15 drops). The reaction mixture was for ½ hour, filtered, and the precipitate washed with ethyl acetate. The organic layer was dried over magnesium sulfate and the salts removed by filtration. The solvent was removed under reduced pressure and the residue dried in vacuo.

The residue was dissolved in methylene chloride and the solution added acetic anhydride (0.11 g, 1.1 mmole). The reaction mixture was stirred at room temperature overnight. The solvent was removed under reduced pressure and the residue dissolved in saturated aqueous potassium carbonate (10 mL), methanol (20 mL), and chloroform (10 mL). The solution was transferred to a separatory funnel. To the solution was added chloroform (10 mL) and aqueous potassium carbonate (10 mL). The layers were separated and the aqueous layer extracted twice with chloroform (10 mL portions). The combined organic layer was dried over magnesium sulfate and the salts removed by filtration. The solvent was removed under reduced pressure and the residue chromatographed on silica (230 to 400 mesh) with chloroform:methanol (9:1) to give the title compound (0.15 g, 5%) as a Clear Oil. $^1$H NMR (300 MHz, CDCl$_3$): δmixture of rotamers: δ0.877 (3H, t, J=6.7 Hz), 1.256 (24H, bs) 1.45 to 1.60 (2H, ml, 1.65 to 1.80 (2H, m) 2.074 and 2.093 (3H, s) 2.221 and 2.252 (6H, s) 2.20 to 2.35 (2H, ml, and 3.15 to 3.40 (2H, m).

IR (neat): 2923, 2653, 1652, and 1456 cm$^{-1}$. Analysis calculated for C$_{23}$H$_{48}$N$_2$O: C, 74.93; H, 13.12; N, 7.59. Found: C, 75.01; H, 13.11; N, 7.53.

EXAMPLE 14

N,N-Dimethyl-N'-hexadecanoyl-1,3-propanediaminehydrochloride (6, hydrochloride salt)

To a solution of 3-dimethylaminopropane (29.7 g, 0.230 mmole) in methylene chloride (500 mL) was added palmitoyl chloride (61.5 g, 0.220 mmole) dropwise over 4 hours. After the addition was complete the solvent was removed under reduced pressure. The residue was refluxed in diethyl ether overnight. The precipitate was filtered and a portion crystallized from ethyl acetate to give the title compound as a white solid. mp. 104°-113° C. $^1$H NMR (300 MHz, DMSO): 0.859 (3H, t, J=6.1 Hz). 1.240 (24H, bs) 1.31 to 1.48 (2H, m) 1.71 to 1.80 (2H, m), 2.059 (2H, t, J=7.4 Hz), 2.713 (6H, s), 2H, t, J=7.8 Hz), 3.00 to 3.10 (2H, m) and 7.076 ppm (1H, s).

Analysis calculated for C$_{21}$H$_{46}$ClN$_2$O: C, 66.89; H, 12.03; N, 7.43; Cl, 9.40. Found: C, 66.95; H, 11.97; N, 7.43; Cl, 9.450.

EXAMPLE 15

N-Hexadecanoyl-N,N',N'-trimethyl-1,3-propanediamine hydrochloride (4, hydrochloride salt)

To a solution of N,N,N'-trimethyl-1,3-propanediamine (25 g, 0.22 mmole) in methylene chloride (500 mL) was added palmitoyl chloride (57 g, 0.20 mmole) dropwise over 4 hours. After the addition was complete the solvent was removed under reduced pressure. The residue was refluxed in diethyl ether (600 mL) overnight. The precipitate was collected and a portion crystallized from ethyl acetate to give the title compound as a white solid. mp. 105.3°-107.9° C. $^1$H NMR (300 MHz, CD3OD): δ0.894 (3H, t, J=6.5 Hz), 1.282 (2H, bs), 1.56 to 1.64 (2H, m), 1.89 to 1.99 (2H, m), 2.411 (2H, t, J=7.1 Hz), 2.873 (6H, s), 3.071 (3H, s) and 3.460 ppm (2H, t, J=6.4 Hz). Analysis calculated for C$_{22}$H$_{48}$ClN$_2$O: C, 67.56; H, 12.12; N, 7.16; Cl, 9.07. Found: C, 67.37; H, 12.03; N, 7.10; Cl, 9.20.

EXAMPLE 16

N-Hexadecanoyl-N,N',N'-trimethyl-1,3-propanediamine (4)

To a solution of N,N,N'-trimethyl-1,3-propanediamine (25 g, 0.22 mmole) in methylene chloride (500 mL) was added palmitoyl chloride (57 g, 0.20 mmole) dropwise over 4 hours. After the addition was complete the solvent was removed under reduced pressure. The residue was refluxed in diethyl ether (600 mL) overnight. A portion of the precipitate was collected by filtration and stirred in saturated aqueous sodium bicarbonate (500 mL) overnight. The reaction mixture was extracted three times with chloroform (500 mL portions). The organic layer was dried over magnesium sulfate and the salts removed by filtration. The solvent was removed under reduced pressure. The residue was Kugelrohr distilled to give the title compound as a clear yellow oil. $^1$H NMR (300 MHz, CDCl$_3$): δrotamers 0.861 (3H, t, J=6.4 Hz), 1.234 (24H, bs) 1.61 to 1.74 (4H, m), 2.196 (6H, s), 2.10 to 2.33 (4H, m) 2.894 and 2.969 (3H, s), 2.767 and 3.139 (2H, t, J=7.3 Hz).

Analysis calculated for C$_{22}$H$_{47}$N$_2$0: C, 74.51; H, 13.08; N, 7.90. Found: C, 74.27; H, 13.02; N, 7.85.

EXAMPLE 17

N,N-Dimethyl-N'-methylethyl-1,3-propanediamine

A solution of 3-dimethylaminopropane (6.25 mL, 49.6 mmole) and a catalytic amount of sodium bicarbonate in dry acetone was stirred at room temperature for 5 days. The salt was removed under reduced pressure. The residue was dissolved in ethanol (40 mL) and cooled in an ice bath. Sodium borohydride (1.72 g, 45.5 mmole) was added to the solution in portions. The reaction mixture was stirred at 0° C. for 4 hours. The reaction mixture was filtered and the solvent removed under reduced pressure. The residue was treated with diethyl ether and the crude product isolated by filtration. $^1$H NMR (300 MHz, D$_2$O): 1.114 (6H, d, J=6.5 Hz), 1.60 to 1.80 (2H, m), 2.236 (6H, s), 2.414 (2H, t, J=7.6 Hz), 2.676 (2H, t, J=7.5 Hz), 2.88 to 3.05 (1H, m). The crude material was carried on to the next step.

EXAMPLE 18

N,N-Dimethyl-N'-propyl-1,3-propanediamine

To a solution of 3-dimethylaminopropane (2.0 g, 20 mmole) in tetrahydrofuran was added propionyl chloride (1.8 mL, 20 mmole) dropwise. The reaction mixture was stirred at room temperature overnight. To the reaction mixture was added a solution of 1M lithium aluminumhydride in tetrahydrofuran (19.5 mL). The reaction mixture was refluxed for 6 hours then cooled to room temperature. The reaction mixture was quenched slowly and sequentially with water (10 drops), 15% aqueous sodium hydroxide (10 drops) and water (30 drops). The precipitate was filtered and the solvent removed under reduced pressure. Excess water was removed by azetroping with benzene. The crude material was carried on to the next step.

EXAMPLE 19

N,N-Dimethyl-N'hexadecanoyl-1,3-propanediamine (6)

To a solution of N,N-dimethyl-1,3-propanediamine (1.00 mL, 7.95 mmole) in methylene chloride (20 mL) was added palmitoyl chloride (2.19 g, 7.97 mmole). The reaction mixture was stirred at room temperature over night. The solvent was removed under reduced pressure and the residue titurated with diethyl ether. The precipitate (2.34 g) was filtered and stirred in saturated aqueous sodium bicarbonate over night. The precipitate was filtered to give the title compound (2.00 g, 74%) as a white solid. Analysis calculated for $C_{21}H_{43}H_2O$ 1.25$H^2O$: C: 69.46; H: 12.91; N: 7.72. Found: C: 69.30 C: 9.46; H: 12.91; N: 7.72 Found: C: 69.30, H: 12.13; H: 12.13; N: 7.58.

EXAMPLE 20

N,N'-Trimethyl-N'-hexadecanoyl-1,3-ethanediamine (25)

A solution of palmitoyl chloride (2.82 g, 10.27 mmole) was added to N,N,N'-trimethylethylene diamine (1.0 g, 9.8 mmole) in ether (20 mL). After stirring overnight at room temperature, the resulting white solid was was collected by vacuum filtration and washed with ether (20 mL) to yield the title compound (3.30 g) as the hydrochoride salt. The salt was recrystallized from isopropanol, then dissolved in methanol (60 mL) chloroform (30 mL) and in aqueous solium hydroxide (27 mL). The solution was transferred to a separatory funnel then chloroform (30 mL) and 1N aqueous sodium hydroxide (30 mL) were added. The aqueous layer was washed twice with chloroform (30 mL) portions. The organic layer was dried over magnesium sulfate and the salts removed by filtration. The solvent was removed under reduced pressure. The residue was dissolved in diethyl ether and a small excess of diazomethane was added to derivatize an impurity which was then removed by flash column chromatography on silica gel, (230–400 mesh) CHCl$_3$ (100%) to CHCl$_3$:MeOH, (9:1) (rf=0.56) to yield the title compound (1.87 g, 56%). $^1$H NMR (300 MHz (300 MHz, CDCl$_3$: rotamers δ3.48, 3.38 (2H, t, J=7 Hz) 3.01, 2.93 (3H, s) 2.46–2.40 (2H, m) 2.29 (6H, s), 1.74–1.62 (2H, m) 1.25 (24H, bs) 0.88 (3H, t J=7 Hz); IR (neat) 3448, 2922, 2852, 2770, 1560, 1462, 1403, 1299, 1174, 1049, 759 cm$^{-1}$.

Anal. calcd for $C_{21}H_{4Cl}N_2O$=C, 74.06; H, 13.02; N, 8.22$^2$. Found—C, 73.96; H, 13.02; N, 8.19.

TABLE 1

$$R_1-\overset{O}{\underset{|}{\underset{R_2}{C}}}-N-(CH_2)_n-R_3$$

| Compound | R$_1$ | R$_2$ | R$_3$ | n | mp °C. | mp °C. salt |
|---|---|---|---|---|---|---|
| 3 | C$_{15}$H$_{31}$ | CH$_3$ | NMe$_2$ | 2 | | 96–98 |
| 4 | C$_{15}$H$_{31}$ | CH$_3$ | NMe$_2$ | 3 | | 105–108 |
| 6 | C$_{15}$H$_{31}$ | H | NMe$_2$ | 3 | | 104–113 |
| 7 | C$_{15}$H$_{31}$ | Et | NMe$_2$ | 3 | | 81–83 |

TABLE 1-continued $$R_1-\overset{O}{\underset{|}{\underset{R_2}{C}}}-N-(CH_2)_n-R_3$$

| Compound | R$_1$ | R$_2$ | R$_3$ | n | mp °C. | mp °C. salt |
|---|---|---|---|---|---|---|
| 8 | C$_{15}$H$_{31}$ | n-C$_3$H$_7$ | NMe$_2$ | 3 | | |
| 9 | C$_{15}$H$_{31}$ | i-C$_3$H$_7$ | NMe$_2$ | 3 | | 80–82 |
| 10 | C$_{15}$H$_{31}$ | H | NEt$_2$ | 3 | | |
| 11 | C$_{15}$H$_{31}$ | H | 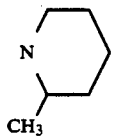 | 3 | 48–50 | |
| 15 | C$_{15}$H$_{31}$ | CH$_3$ | $\overset{\oplus}{N}Me_3 I^\ominus$ | 3 | 117–119 | |
| 16 | C$_{15}$H$_{31}$ | CH$_3$ | 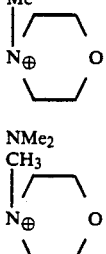 | 3 | 95–96 | |
| 20 | CH$_3$ | C$_{16}$H$_{33}$ | NMe$_2$ | 3 | | |
| 22 | C$_{15}$H$_{31}$ | PhCH$_2$ | CH$_3$ 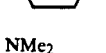 | 3 | | |
| 25 | C$_{15}$H$_{31}$ | CH$_3$ | NMe$_2$ | 2 | 96–98 | |
| 26 | C$_{12}$H$_{25}$ | CH$_3$ | NPr$_2$ | 4 | | |
| 27 | C$_{13}$H$_{27}$ | CH$_3$ | 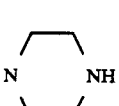 | 5 | | |
| 28 | C$_{14}$H$_{29}$ | CH$_3$ | (piperazine) | 3 | | |

EXAMPLE 21

Protein Kinase C Inhibition

The protein kinase C (PKC) assay is designed to duplicate the in vivo conditions required for protein kinase C function. Therefore, pH, salt and cofactor concentrations are similar to physiologic levels. Histone H1 (lysine rich) is used in the assay as the phosphorylation acceptor protein because it is readily available and serves as a good substrate for protein kinase C. The enzyme is prepared from rat brain and is purified to apparent homogeneity as determined by a single band on silver stained SDS-polyacrylamide. Studies on the mechanism of regulation of protein kinase C by phospholipids, DAG and Ca$^{+2}$ have been hampered by the physical properties of the lipid cofactors. In the screening assay, phosphatidylserine (PS) and DAG are cosonicated to form unilamellar and multilamellar vesicles. The concentration of lipids in the assay are suboptimal to maximize the detection potential of the assay for inhibitors. Potential inhibitor compounds are added to the assay in dimethylsulfoxide at three concentrations to give final inhibitor concentrations of 4.3, 43 and 218

μM, respectively. The assay is started with the addition of enzyme and stopped after 10 min by the addition of 25% trichloroacetic acid (TCA) and 1.0 mg/ml bovine serum albumin (BSA). The radioactive histone product is retained and washed on glass fiber filters that allow the unreacted $^{32}$P-ATP to pass through. The amount of phosphorylation is determined by the radioactivity measured in a scintillation counter. Controls are included in every assay to measure background activity in the absence of enzyme, activity in the absence of lipids and the maximum enzyme activity with saturating levels of the activator lipids. Assay components and concentrations are given in Table 2.

TABLE 2

| Assay Component | Concentration |
| --- | --- |
| Hepes pH 7.5 | 20 μM |
| MgCl$_2$ | 20 μM |
| CaCl$_2$ | 100 μM |
| EGTA | 95 μM |
| Histone H1 | 200 μg/ml |
| Phosphatidylserine | 40 μg/ml |
| Diacylglycerol | 1.8 μg/ml |
| Protein Kinase C | 0.6 μg/ml |
| γ-$^{32}$P-ATP | 20 μM |

Results of the protein kinase C assay are shown in Table 3. Both the free base and the HCl salt were tested. Results are shown as IC$_{50}$, which is the concentration of test compound needed to inhibit 50% of the protein kinase C activity as compared with levels of protein kinase C activity in controls. Compounds of the invention were able to effectively inhibit protein kinase activity at levels ranging from 22 to 146 μM.

TABLE 3

| | IC$_{50}$ (μM) PKC | |
| --- | --- | --- |
| Compound | free base | HCl salt |
| 3 | 40 | 66 |
| 4 | 107 | 57 |
| 6 | 50 | 50 |
| 7 | 50 | 38 |
| 8 | 131 | 48 |
| 9 | 146 | 130 |
| 10 | 131 | |
| 11 | 130 | 66 |
| 15 | 24 | |
| 16 | 22 | |
| 20 | 69 | 44 |
| 22 | 45 | |
| 25 | 92 | 100 |

EXAMPLE 22 cAMP-Dependent Protein Kinase (PKA) Assay

Compound found to be inhibitors of protein kinase C are tested for inhibitory activity against protein kinase (PKA). This enzyme, like protein kinase C, plays an important role in cell-cell communication and is activated by a second messenger, cAMP. Secondary screening against PKA is useful for ascertaining the selectivity of the compounds of the invention. The standard assay conditions are given in Table 4. The catalytic subunit of PKA (Sigma Chemical Company, St. Louis, Mo.) is mixed with buffer before addition of the inhibitor in dimethylsulfoxide (DMSO). The assay is started by the addition of 32P-ATP and the reaction is allowed to proceed for 10 min before stopping with 25% trichloroacetic acid (TCA) and 1.0 mg/ml bovine serum albumin (BSA). The phosphorylated protein is isolated by filtration and the radioactivity is counted in a beta scintillation counter.

TABLE 4

| Assay Components | Concentration |
| --- | --- |
| Hepes pH 7.5 | 20 μM |
| Histone H1 | 200 μg/ml |
| Dithiothreitol | 132 μg/ml |
| Protein Kinase A | 2.6 μg/ml |
| γ-$^{32}$-ATP | 20 μM |

Results of the PKA assay are shown in Table 5. As shown in Table 5, the tested compounds inhibited protein kinase at levels ranging from 67 μM to greater than 218 μM. Since the levels of compound needed to inhibit fifty percent of protein kinase C activity were significantly lower than the amounts needed to inhibit fifty percent of the protein kinase activity, the compounds of the invention should have minimal effect in the metabolic pathways associated with stimulation of protein kinase by cAMP.

TABLE 5

| Compound free base | PKA IC$_{50}$ (μM) |
| --- | --- |
| 4 | 90 |
| 6 | 140 |
| 7 | 119 |
| 8 | >218 |
| 9 | 172 |
| 10 | >218 |
| 11 | >217.50 |
| 16 | 131 |
| 20 | 67 |
| 22 | <44 |
| 25 | >218 |

EXAMPLE 23

Human Tumor Cell Growth Inhibition

MCF-7 a human breast tumor cell line and MCF-7/ADR an adriamycin resistant line of MCF-7 cells were obtained from the National Cancer Institute, Frederick, Md. CEM cells (ATCC accession number CCL 119) were obtained from the American Type Culture Collection, Rockville, Md. Human tumor cells are trypsinized (0.05% trypsin, GIBCO), counted with a hemacytometer and seeded at a concentration of 10,000 cells/well in a 96 well microtiter plate. After allowing cells to attach to the surface overnight, the culture medium is aspirated and replaced with 100 μl of fresh medium. Test agents are diluted to determine dose response at 2× final concentration and added in quadruplicate at 100 μl/well to bring the total volume of each well to 200 μl. The microtiter plate is then incubated at 37° C. 5% CO$_2$ overnight (18–24 hrs) before $^3$H-thymidine is added at a concentration of 0.5 μCi/well in 50 μl culture medium. The plate is incubated again for 4 hrs under the same conditions as above. Supernatant is then aspirated and 50 μl trypsin (0.05%, GIBCO) is added to each well. Cells are checked microscopically to determine detachment from surfaces, and plates are then harvested with a cell harvester (PHD, Cambridge Technology, Inc.) Filter papers corresponding to wells are placed in scintillation vials and counted to determine the amount of $^3$H-thymidine incorporated by the cells. Test agent response is compared to a positive control of cell wells with culture media only to determine the IC$_{50}$. IC$_{50}$ is the concentration of test compound required to inhibit fifty per cent of the incorporation of $^3$H-thymidine into proliferating cells not exposed to test agent. Uptake of $^3$H-thymidine is a standard test for measuring the metabolism of cells. Cells which are actively proliferating take up $^3$H-thymidine, whereas cells that are not proliferating take up $^3$H-thymidine at much slower rates or not at all. Test agents that inhibit the uptake of $^3$H-thymidine thus slow the growth of cells.

As shown in Table 6, compounds 4 and 6 were able to effectively inhibit growth of MCF-7 cells at micromolar concentrations.

TABLE 6

| Compound | IC$_{50}$ ($\mu$M) MCF-7 (salt) | MCF-7/ADR (salt) |
|---|---|---|
| 4 | 1.50 (2.90) | |
| 6 | 4.50 (3.50) | |
| 8 | 9.70 | |
| 9 | 5.10 | |
| 11 | 4.10 | 2.60 |
| 15 | 5.00 | |
| 16 | 19.30 | >25.00 |
| 22 | 15.40 | |

EXAMPLE 24

Human Keratinocyte Inhibition

Proliferating keratinocytes (NHEK cells purchased from Clonetics, Inc., San Diego, Calif.) in second passage were grown in Keratinocyte Growth Medium (KGM) (Clonetics, Inc.) Cells are trypsinized (0.025% trypsin, Clonetics), counted with a hemacytometer (Scientific Products), and seeded at a concentration of 2,500 cells/well in a 96 well microtiter plate. After allowing cells to attach to the surface overnight, the culture medium is aspirated and replaced with 100 $\mu$l of fresh KGM. Test agents are evaluated and IC$_{50}$'s are determined according to the $^3$H-thymidine incorporation procedures described as in Example 23. IC$_{50}$ is the concentration of test compound required to inhibit fifty percent of the incorporation of $^3$H-thymidine into proliferating cells not exposed to test agent.

| Keratinocyte Inhibition Assay | | |
|---|---|---|
| Compound | NHEK IC$_{50}$ ($\mu$M) | (salt) |
| 4 | 0.80 | (2.40) |
| 6 | | (0.78) |
| 8 | 1.03 | |
| 9 | 0.14 | |
| 10 | 1.56 | |
| 15 | 3.30 | |
| 16 | 1.40 | |
| 20 | 1.30 | |
| 22 | 1.60 | |

EXAMPLE 25

Neutrophil Superoxide Anion (O$_2^-$) Release Assay

Neutrophils are isolated form whole blood collected from human volunteers. All reagent materials are obtained from Sigma Chemical Company with the exception of isotonic saline (Travenol Laboratories, Inc., Deerfield, Ill.) and lymphocyte separation medium (Organon Teknika, Durham, N.C.).

Neutrophil Isolation

Whole blood is drawn and mixed with sodium heparin (final conc. 10 units/ml) to prevent clotting. An equal volume of dextran (3.0%) in isotonic saline is added, mixed, and allowed to settle for 30 min to bind red blood cells (RBC). Supernatant is removed, underlayered with lymphocyte separation medium and centrifuged for 40 min at 400 xg in a centrifuge (Beckman GPR, Norcross, Ga). The pellet is alternately resuspended in 0.2% and 1.6% NaCl to lyse RBCs before washing with Hank's Balanced Salt Solution (HBSS). The washed pellet is resuspended in 10 mL HBSS and placed on ice before counting on a hemacytometer.

Assay Procedure

The neutrophil cell concentration is adjusted to 2×10$^6$ cells/ml with HBSS before adding 0.8 mL cells to 12×75 mm polypropylene test tubes (Fisher Scientific). Test agents are diluted to determine dose response and added at 10× final concentration at a volume of 0.1 mL/tube in duplicate. Then 10× concentrations of cytochrome C (15 mg/ml) with catalase (3000 units/ml) either alone or containing 25 ng/ml phorbol 12-myristate 13-acetate (PMA) are added at a volume of 0.1 mL/tube and incubated at 37° C. for 30 min before stopping the reaction by placing tubes on ice. Tubes are then centrifuged at 900 xg for 10 min, 0.5 mL supernatant is removed and added to 0.5 mL H$_2$O in a microcuvette. Optical density (OD) of cytochrome c is read in a spectrophotometer (Shimadzu) at 550 nm. The $\Delta$OD of cytochrome c is obtained between PMA-stimulated and non-stimulated tubes, and the dose responses of the test agents are compared to the positive controls (which contain HBSS in place of test agents). PMA stimulates O$_2^-$ production which reduces cytochrome c. Reducing cytochrome c increases its absorbance, and the change in OD of cytochrome c is proportional to the amount of O$_2^-$ produced by PMA stimulation. Inhibition of the O$_2^-$ burst by test compounds of the invention is seen as a reduction in the change in optical density. Inhibition is expressed as IC$_{50}$ $\mu$M and is the amount of test compound that will inhibit fifty percent of the PMA-stimulated respiratory outburst, i.e. O$_2^-$ production.

Compounds 4 and 6, as well as the HCl salts of compounds 4 and 6, were able to inhibit O$_2^-$ production by PMA-stimulated neutrophils at micromolar concentrations.

TABLE 7

| | Neutrophil Superoxide Release | |
|---|---|---|
| Compound | IC$_{50}$ ($\mu$M) | (salt) |
| 4 | 45.00 | (2.39) |
| 6 | 2.32 | (2.80) |
| 8 | 2.90 | |
| 9 | 0.90 | |
| 11 | 1.80 | |
| 20 | 1.10 | |

We claim:

1. A method of inhibiting protein kinase C which comprises contacting protein kinase C with an inhibitory amount of a compound having the formula

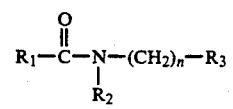

wherein R$_1$ is C$_8$ through C$_{15}$ alkyl; R$_2$ is H, C$_1$ through C$_{10}$ alkyl, or benzyl; R$_3$ is N-heterocyclic, N-alkyl-heterocyclic, quaternized N-heterocyclic, NR$_4$R$_5$ or $N^+R_4R_5R_6X^-$; $R_4$, $R_5$ and $R_6$ are independently $C_1$ through $C_{10}$ alkyl; n is 2, 3, 4, or 5; and X is an anion.

2. The method of claim 1 wherein $R_1$ is $C_{12}$ through $C_{15}$ alkyl; $R_2$ is H, $C_1$ through $C_5$ alkyl, or benzyl; $R_3$ is N-heterocyclic, N-alkylheterocyclic or quaternized N-heterocyclic, $NR_4R_5$ or $N^+R_4R_5R_6X^-$; $R_4$, $R_5$ and $R_6$ are independently $C_1$ through $C_{10}$ alkyl; n is 2, 3, 4, or 5; and X is an anion.

3. The method of claim 2 wherein $R_1$ is $C_{12}$ through $C_{15}$ alkyl; $R_2$ is H, methyl, ethyl, propyl or benzyl; $R_3$ is N-methylmorpholino, or $NR_4R_5$; $R_4$ and $R_5$ are independently methyl or ethyl; and n is 2 or 3.

4. A method of inhibiting protein kinase C which comprises contacting protein kinase C with an inhibitory amount of a compound having the formula

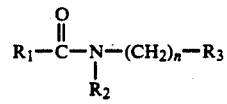

wherein $R_1$ is $C_1$ through $C_3$ alkyl; $R_2$ is $C_8$ through $C_{15}$ alkyl; $R_3$ is N-heterocyclic, N-alkylheterocyclic, quaternized N-heterocyclic, $NR_4R_5$ or $N^+R_4R_5R_6X^-$; $R_4$, $R_5$ and $R_6$ are independently $C_1$ through $C_{10}$ alkyl; n is 2, 3, 4, or 5; and X ia an anion.

5. The method of claim 4 wherein $R_1$ is methyl; $R_2$ is $C_{16}$ alkyl; $R_3$ is N-methyl morpholino, or $NR_4R_5$; $R_4$ and $R_5$ are methyl or ethyl; n is 2 or 3.

* * * * *